United States Patent
Villani

[11] Patent Number: 5,848,989
[45] Date of Patent: Dec. 15, 1998

[54] IMPLANTABLE PORT WITH LOW PROFILE HOUSING FOR DELIVERY/COLLECTION OF FLUIDS AND IMPLANTATION METHOD

[75] Inventor: Giuseppe Villani, Shrewsbury, Mass.

[73] Assignee: DaVinci Biomedical Research Products, Inc., Shrewsbury, Mass.

[21] Appl. No.: 869,636

[22] Filed: Jun. 5, 1997

[51] Int. Cl.[6] .................................................. A61M 5/00
[52] U.S. Cl. ............................................. 604/93; 604/175
[58] Field of Search ................................. 604/93, 82, 83, 604/86, 167, 175, 280, 283

[56] References Cited

U.S. PATENT DOCUMENTS

| | | | |
|---|---|---|---|
| 3,310,051 | 3/1967 | Schulte | 128/216 |
| 3,640,269 | 2/1972 | Delgado | 128/2 R |
| 3,783,868 | 1/1974 | Bokros | 128/260 |
| 3,971,376 | 7/1976 | Wichterle | 128/260 |
| 4,464,178 | 8/1984 | Dalton | 604/174 |
| 4,781,695 | 11/1988 | Dalton | 604/175 |
| 4,915,690 | 4/1990 | Cone et al. | 604/93 |
| 5,053,013 | 10/1991 | Ensminger et al. | 604/167 |
| 5,057,084 | 10/1991 | Ensminger et al. | 604/167 |
| 5,074,847 | 12/1991 | Greenwell et al. | 604/174 |
| 5,090,954 | 2/1992 | Geary | 604/29 |
| 5,092,849 | 3/1992 | Sampson | 604/175 |
| 5,108,377 | 4/1992 | Cone et al. | 604/175 |
| 5,180,365 | 1/1993 | Ensminger et al. | 604/93 |
| 5,226,879 | 7/1993 | Ensminger et al. | 604/93 |
| 5,263,930 | 11/1993 | Ensminger | 604/93 |
| 5,281,199 | 1/1994 | Ensminger et al. | 604/93 |
| 5,312,377 | 5/1994 | Dalton | 604/283 |
| 5,350,360 | 9/1994 | Ensminger et al. | 604/93 |
| 5,356,381 | 10/1994 | Ensminger et al. | 604/93 |
| 5,387,192 | 2/1995 | Glantz et al. | 604/93 |
| 5,417,656 | 5/1995 | Ensminger et al. | 604/93 |
| 5,503,630 | 4/1996 | Ensminger et al. | 604/93 |
| 5,520,643 | 5/1996 | Ensminger et al. | 604/93 |
| 5,527,277 | 6/1996 | Ensminger et al. | 604/93 |
| 5,527,278 | 6/1996 | Ensminger et al. | 604/93 |
| 5,531,684 | 7/1996 | Ensminger et al. | 604/93 |
| 5,542,923 | 8/1996 | Ensminger et al. | 604/93 |
| 5,554,117 | 9/1996 | Ensminger et al. | 604/93 |
| 5,556,381 | 9/1996 | Ensminger et al. | 604/93 |
| 5,558,641 | 9/1996 | Glantz et al. | 604/93 |
| 5,562,618 | 10/1996 | Cai et al. | 604/93 |
| 5,607,393 | 3/1997 | Ensminger et al. | 604/93 |

*Primary Examiner*—John D. Yasko
*Attorney, Agent, or Firm*—Volpe and Koenig, P.C.

[57] ABSTRACT

An implantable port having a low profile housing for delivery/collection of fluids into and out of a body. The low profile housing includes a selectively configured open flared end which serves to guide a needle directly into an inlet defined in the housing. A septum is mounted in the port's inlet via a hollow core which is inserted into the housing in a compression fit. The septum is selectively compressed to reduce its deflection characteristic to minimize backflow of fluid into the port. A catheter of selected size may be connected to a port outlet to direct fluid to a desired location. The implant may be configured to have multiple ports or to have a specially adapted outlet for cranial mounting. An implantation method is also provided where only the leading flared end of the port is sutured to the fascia. Where the port is implanted in a laboratory animal, preferably dissolvable sutures are used to permit migration of the port to accommodate the animal's growth.

27 Claims, 3 Drawing Sheets

IMPLANTABLE PORT WITH LOW PROFILE HOUSING FOR DELIVERY/COLLECTION OF FLUIDS AND IMPLANTATION METHOD

BACKGROUND OF THE INVENTION

1. Field of the Invention

The present invention generally relates to implantable ports, specifically implantable ports having a puncturable, self-sealing septum, for controlling delivery/collection of fluids/compounds into and out of a body and an implantation method.

2. Description of the Prior Art

There are many known methods and devices for delivering and collecting fluids from a body. Implanted ports are commonly used with laboratory animals, but there are also a variety of medical applications for human implant ports.

With respect to implants, typically, a port device is implanted between the skin and fascia of a body. One class of implants have an inlet with a puncturable, self-sealing septum or diaphragm mounted in the mouth of the inlet and an outlet connected to or for connection with a catheter of a selected size. A needle, such as a hypodermic needle, is advanced through the septum of the implantable device for delivering fluids to the blood stream or to an internal body cavity for selective regional therapy.

The implantable device may-be filled from time to time by a hypodermic injection with a single dose or multi-dose quantity of a drug. The drug may-be delivered quickly or delivered slowly and continuously. A catheter or drug permeable membrane may be connected to the outlet of the port to direct the injected fluid to a desired site in the body requiring medication.

The implantable device may also be used to obtain samples of fluids from selected sites in the body. Fluid may be periodically withdrawn from an implanted port by using a hypodermic syringe attached to a needle.

U.S. Pat. No. 4,781,695 (Dalton '695) and U.S. Pat. No. 4,464,178 (Dalton '178) disclose ports which are implanted into a subject. The Dalton port includes a relatively large septum which makes the device relatively large. The Dalton '695 port requires an internal bent tube which increases the height of the port. As the height of the port increases, there is an increased risk that bacteria will come between the skin and the fascia due to the space between the skin and the fascia after implantation of the port into the subject. In addition, it is difficult to implant and suture the Dalton drug depot to the fascia without making large cuts in the skin, which also increases the risk of infection.

U.S. Pat. No. 5,092,849 also discloses an implantable device for delivering and collecting fluids. The device includes a puncturable, self-sealing septum which provides a 0.15–0.20 inch target area for a needle. In addition, where means for affixing the device to the fascia are provided, the suture holes are far apart requiring large cuts on the subject during implantation of the device. This increases the risk of infection.

With the prior art devices, leakage and backwash become problematic particularly after the inlet septum has been punctured multiple times. Backwash occurs when the needle is extracted from the device causing the septum to be deflected outwardly. Outward deflection of the septum when the needle is extracted removes fluid from the body into the open end of the catheter which can cause clogging. After multiple uses, when a needle is inserted, the needle may also inwardly deflect the septum which thereafter exacerbates the problem of backwash when the needle is removed. Multiple punctures may also cause leakage of the subject's fluids through the inlet of the drug depot.

It would be desirous to provide a relatively compact, easily manufacturable and implantable port having an easily locatable inlet having a septum with enhanced deflection and leakage resistant characteristics.

SUMMARY OF THE INVENTION

An implantable port for delivering and collecting fluids in a body is provided. The port has a hollow housing in which a relatively small inlet is defined by a radially inwardly projecting lip which is substantially perpendicular to the base of the housing. A septum is mounted in the mouth of the housing inlet by means of a hollow core which is inserted within the housing in a compression fit. The core axially compresses the septum against the housing inlet lip. The housing has a selectively configured open flared end extending in front of the inlet having a surface which is shaped to guide a needle to the port inlet and into the septum.

The flared end guide design of the housing permits the use of relatively small inlet sizes of less than 0.15 in. in diameter. Preferably, the guide surface of the open flared end is at least two to six times as wide as the diameter of the inlet and extends at least twice the diameter of the inlet in front of the inlet.

The relatively small target area defined by the inlet enhances the septum's resistance to deflection and leakage. For inlet sizes, i.e. septum target areas, greater than 0.1 in. in diameter, the inlet size is preferably selected to be less than four times the interior diameter of the catheter with which the implant is used. For example an inlet size of 0.125 in. permits use of a No. 5 French polyurethane catheter having a 0.040 in. internal diameter without significant backwash problems. For inlet sizes, i.e. septum target areas, less than 0.1 in. in diameter, the problems associated with septum deflection virtually disappear. For example an inlet size of 0.090 in. permits use of a No. 2 French polyurethane catheter having a 0.015 in. internal diameter without significant backwash problems even though the inlet diameter is six times the internal diameter of the catheter. The relatively small inlet size also facilitates use of a low profile housing having a height not greater than three times the diameter of the inlet.

Preferably the port has a generally tapered body leading to its flared end which facilitates implantation via a relatively small incision. The open flared end also provides a beneficial locus for suturing the implant to the fascia without the need for an enlarged incision. Where the port is implanted in a young laboratory animal, dissolvable sutures are used to permit migration of the port to accommodate the animal's growth.

It is an object of the present invention to provide an implantable port having a low profile housing for repeatedly delivering and collecting fluids to and from a body without the risk of infection caused by backwash, leakage, dead space and unnecessary surgical cuts.

It is a further object to provide an implantable port with an open, flared needle guide which also provides an improved means for attaching the implant to the fascia.

Other objects and advantages will become apparent to those skilled in the art after reading the detailed description of the preferred embodiments.

DESCRIPTION OF THE PREFERRED EMBODIMENTS

Figure 1:
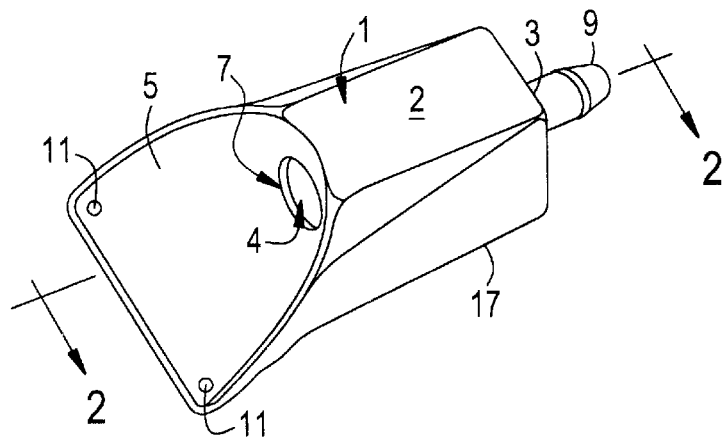
FIG. 1 is a top perspective view of a low profile single catheter port of a first embodiment of the present invention.
Figure 2:
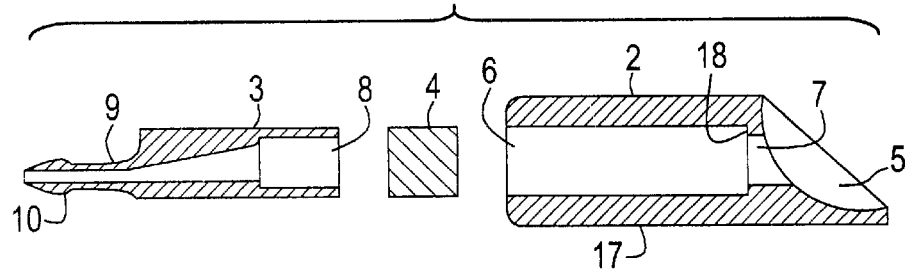
FIG. 2 is an exploded section view showing three components of the low profile single catheter port along line 2—2 in FIG. 1.
Figure 3:
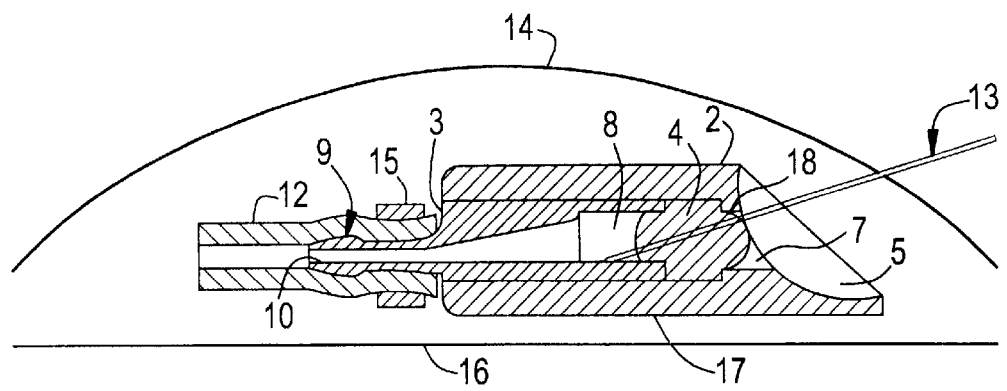
FIG. 3 is the section view of FIG. 2 of the low profile single catheter port implanted in a body.

The preferred embodiments are described with reference to drawing figures wherein like numerals represent like elements throughout. FIGS. 1–3 disclose a first embodiment of the present invention. A single catheter port 1 includes a housing 2, a hollow core 3 and a self sealing, puncturable septum 4 which is mounted in the housing 2 via the hollow core 3.

The housing 2 has a relatively flat base 17 with an open flared end 5 and an enclosed, hollow body portion 6. A radially inwardly projecting lip 18 defines an inlet 7 of a selected dimension which is substantially perpendicular to the housing's flat base and provides access to the hollow body portion 6 from the flared end 5. The flared end 5 has an upper surface selectively shaped and tapered toward the inlet 7 which serves to guide a needle 13 to the inlet 7 during use thereby permitting the inlet 7 to be relatively small in size.

Preferably, the inlet 7 is less than 0.15 in. in diameter which in turn permits the housing 2 to have a very low profile having a height less than three times the height of the inlet 7. To facilitate the location of the inlet 7, the guide surface of the open flared end 5 is preferably at least two to six times as wide as the width of the inlet 7 and extends at least twice the width of the inlet 7 in front of the inlet. In one example a housing 2 has inlet 7 0.125 ins. in diameter, a height of 0.312 in. and a guide surface 0.640 in. wide extending 0.339 in. in front of said inlet 7; in another example a housing 2 has an inlet 7 0.090 in. in diameter, a height of 0.225 in. and a guide surface 0.412 in. wide extending 0.216 in. in front of said inlet 7.

The hollow core 3 is generally cylindrically shaped for mating insertion into the hollow body portion 6 of the housing 2. Preferably, the hollow body portion 6 has a cylindrical interior with an interior diameter which is slightly smaller than the exterior diameter of the hollow core 3 such that an interference fit is defined between the two components. Preferably, the difference in diameters is 0.002±0.0005 in., but may vary dependent upon the materials used. The interference fit is strong enough to avoid inadvertent separation of the assembled components, preferably a force of between 25–53 lbs. is required to separate the hollow core 3 from the housing 2.

Preferably, both the housing 2 and core 3 are made of ULTEM® 1000 polyetherimide available from General Electric. Other biocompatible plastic or metal materials for one or both parts may be employed, for example: polysulfone, stainless steel, or titanium.

The hollow core 3 includes a reservoir 8 which tapers downwardly to a straight port outlet 9 defined on the lower rear portion of the hollow core 3. The straight flat communication of the outlet 9 to the reservoir 8 retards the tendency for pooling of fluids within the reservoir 8. Also, the location of the outlet 9 proximate the bottom of the hollow core 3 reduces the amount of potential dead space which would occur if the outlet 9 were axially aligned with the reservoir 8 and inlet 7. The single catheter outlet 9, being close to the fascia 16, decreases the risk of infection.

In its uncompressed state, shown in FIG. 2, the septum 4 is preferably cylindrically shaped having an uncompressed thickness of about 0.125 in. and a diameter approximately equal to the interior diameter of the hollow portion 6 of the housing 2. The septum 4 is preferably made of silicone.

The septum 4 is mounted in the mouth of the housing inlet 7 by inserting the septum 4 within the hollow housing portion 6 to abut the inwardly projecting lip 18 which defines the inlet 7 and then inserting hollow core 3 within the hollow portion 6 of the housing 2 to axially compress the septum 4 by about 0.020–0.025 in. around its edge. The compression is sufficient to cause the septum 4 to deform and project into the inlet 7 and also into the reservoir 8 of the core 3. The compression reduces the natural deflection characteristics of the septum 4 and enhances its self sealing characteristics. In this approximate range of compression, where the septum target area is less than 0.15 in., a needle 13 can be inserted through and extracted from a septum 1,400–1,650 times before leakage of the septum 4. To little compression results in leakage problems, too much compression causes the housing to split.

As best seen in FIG. 3, when the single catheter port 1 is in use, a catheter 12 of a selected size is secured to the outlet 9 of the hollow core 3 which projects from the lower edge of the back of the single catheter port 1. Preferably, if the inlet diameter is greater than 0.1 in., the interior diameter of the catheter 12 is at least four times as large as the inlet diameter. For example an inlet size of 0.125 in. permits use of a No. 5 French polyurethane catheter having a 0.040 in. internal diameter without significant backwash problems. For inlet diameters of 0.1 in. or less, even relatively smaller sized catheters may be used. For example an inlet size of 0.090 in. permits use of a No. 2 French polyurethane catheter having a 0.015 in. internal diameter without significant backwash problems even though the inlet diameter is six times the internal diameter of the catheter 12.

Connection of the catheter 12 may be made at anytime, but will usually be made prior to or during implantation. Preferably the outlet 9 is configured with a nipple 10 over which the catheter 12 is slid. A retaining ring 15 is then slid over the catheter 12 and the outlet nipple 10 to secure the catheter 12 onto the outlet 9.

Generally the open end of the catheter 12 is specially prepared by milling or the like to be extremely smooth in order to avoid infection or degradation. Accordingly, if adjustment to the length of the catheter 12 is required, it is preferably made by cutting the end of the catheter 12 which is to be connected to the straight port outlet 9 to maintain the integrity of the open end of the catheter 12.

The tapered configuration of the port 1 facilitates its implantation and the housing's flared end 5 provides a suitable stable locus for securing the implant. Accordingly, suture apertures 11 are defined on opposing sides of the flared end 5 of the housing 2.

During implantation, an incision is made into the skin 14 of the body slightly greater than the width of the narrow end of the port 1. The single catheter port 1 is introduced into the incision narrow end first. Normally, the catheter 12 will be connected to the single catheter port 12 prior to insertion of the single catheter port 1 through the incision; the catheter 12 having been implanted in a conventional manner. After insertion of the single catheter port 1, sutures are applied to the port's suture apertures 11 to secure the single catheter port 1 in position, usually on the fascia 16. The incision is then closed in a conventional manner. By only requiring sutures on the leading edge of the single catheter port 1, the size of the incision is minimized allowing the wound caused by the incision to more easily heal.

After implantation, the single catheter port 1 is completely covered by the skin 14 and is not visible. Use of the single catheter port 1 is made by inserting a needle 13 through the skin 14 and the septum 4 to deliver or extract fluids from the reservoir 8. The tapered shape of the single catheter housing 2 facilitates the rough location of the single catheter port 1 through feeling the single catheter port 1 through the body's skin. The flared open end 5 of the housing 2 effectively guides a needle 13 to the inlet 7 so that the needle may penetrate the septum 4. The flared end reduces the chance of inadvertently puncturing the fingers of a person grasping the single catheter port 1 to make the injection which is particularly beneficial in a laboratory setting where technicians are required to perform a high volume of injections in any given time period.

As best seen in FIG. 3, the configuration of the flared end 5 and the substantially vertically orientation of the septum 4 in the housing inlet 7, permits a needle 13 to penetrate the septum 4 at an angle of up to about 40° above the horizontal plane on which the single catheter port 1 resides.

Figure 4:
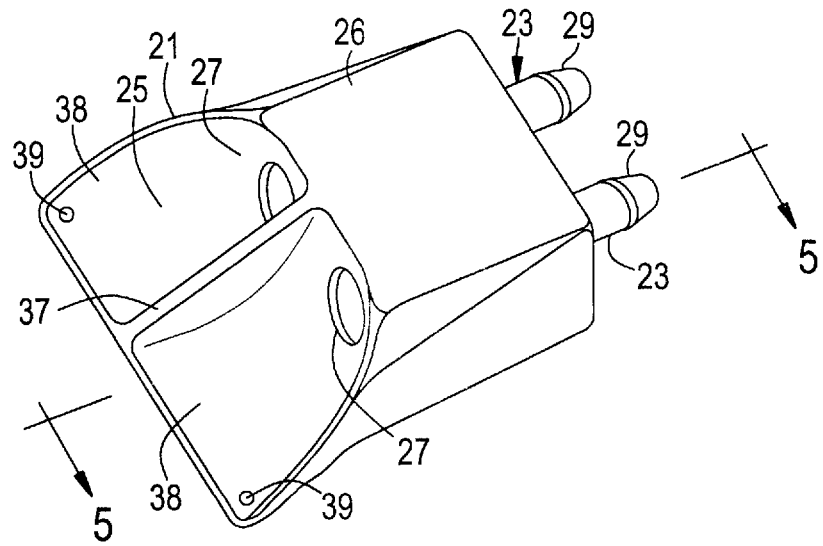
FIG. 4 is a perspective view of a low profile dual catheter port of a second embodiment of the present invention.
Figure 5:
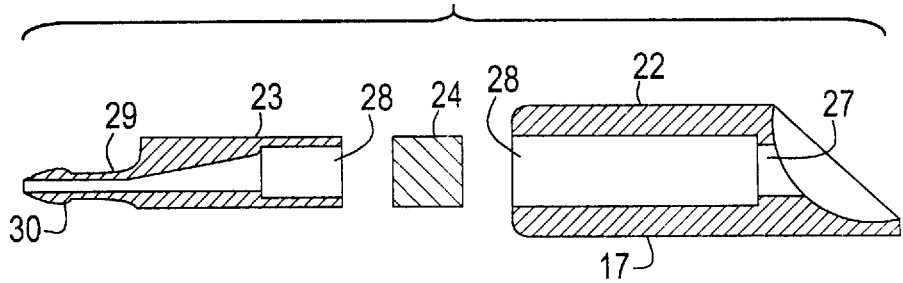
FIG. 5 is an exploded section view showing three components of the low profile dual catheter port along line 5—5 in FIG. 4.
Figure 6:
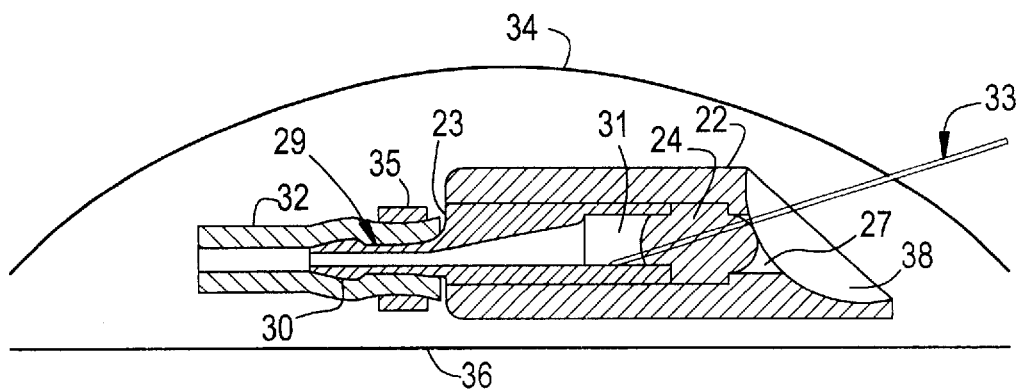
FIG. 6 is the section view of FIG. 5 of the low profile dual catheter port implanted in a body.

FIGS. 4–6 illustrate a second embodiment of an implantable port 21 in which access for two catheters 32 is provided. The dual catheter port 21 includes a housing 22 having an open flared end 25 and an enclosed portion 26. Two inlets 27 are provided which provide access from the flared end 25 to two core receiving chambers 28. A septum 24 is mounted in the mouth of each inlet 27 by inserting a selectively configured hollow core 23 in an interference fit in each of the internal chambers 28 as described above in conjunction with the first embodiment of the invention.

Each hollow core 23 includes a port outlet 29 having a nipple 30. Each port outlet 29 leads straight out from the bottom of a reservoir 31 defined in each core 23. A catheter 32 of a selected size may be mounted on each port outlet 29 and secured by a retaining ring 35. When implanted under the skin 34 the port outlets 29 are proximate the skin's fascia 36 so that there is minimal dead space which decreases the risk of infection.

As best seen in FIG. 4, the flared end 25 of the housing 22 is divided by a partition 37 to define two selectively shaped guide surfaces 38. Each guide surface 38 extends in front of a respective inlet 27 at least twice the inlet's width and is at least two and one half times the inlet's width at the leading edge of the flared end 25. Each guide surface 38 is shaped to guide a needle 33 to the respective inlet 27 for insertion through the septum 24 disposed therein.

The leading edge of the flared end 25 includes suture holes 39 to anchor the dual catheter port 21 onto the skin's fascia 36. The suture holes 39 are positioned to minimize the surgical cuts necessary to implant the dual catheter port 21 to minimize the risk of infection.

Figure 7:
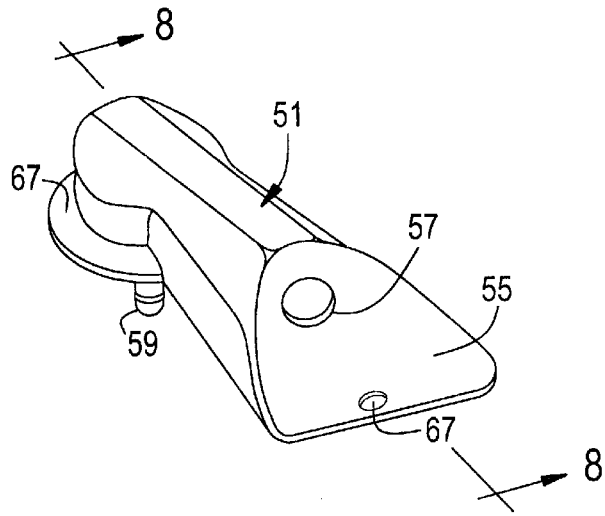
FIG. 7 is a top perspective view of a low profile neurocatheter implantable port of a third embodiment of the present invention.
Figure 8:
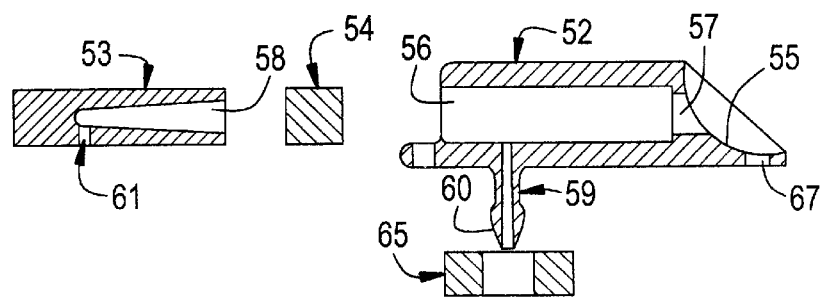
FIG. 8 is an exploded section view showing four components of the low profile neurocatheter port along line 8—8 in FIG. 7.
Figure 9:
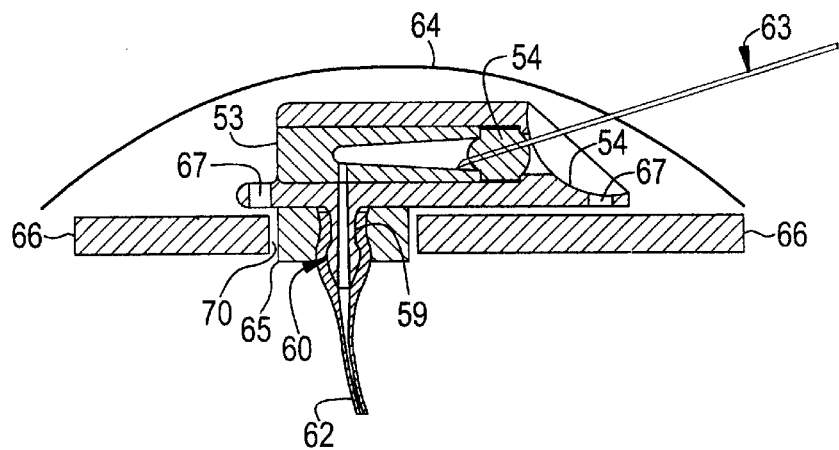
FIG. 9 is the section view of FIG. 8 of the low profile neurocatheter port implanted in a body.

FIGS. 7–9 disclose a third embodiment of the present invention. A neurocatheter port 51 includes a housing 52, a hollow core 53 and a septum 54. The port housing 52 includes an open flared end 55, an enclosed housing portion 56, and an inlet 57 which leads from the flared end 55 into the interior of the enclosed housing portion 56. The hollow core 53 compressively maintains the septum 54 in the mouth of the inlet 57, being inserted with an interference fit with the interior of the enclosed housing portion 56 in the same manner as described with respect to the first embodiment. The flared end 55 includes a surface shaped to guide a needle 63 to the inlet 57 for insertion through the septum 54 disposed therein.

In the neurocatheter port 51, a reservoir 58 is defined in the hollow core 53. A port outlet 59 which has a nipple 60 projects perpendicularly downwardly from the flat base of the port housing 52. An aperture 61 is defined in the bottom of the hollow core 53 and is positioned to be in communication with the port outlet 59 when the component parts are assembled such that fluid injected into the reservoir 58 flows to the outlet 59. A neurocatheter 62 is connected to the port outlet 59 and maintained by a retaining ring 65.

The neurocatheter port 51 is implanted under the skin 64 and is secured to a subject's skull 66 via screws (not shown). Screw holes 67 are provided at opposing ends of the neurocatheter port 51 for this purpose. During implantation, an incision is made though the skin 64 and a hole 70 is drilled in the skull 66 though which the catheter and the outlet are inserted.

Retaining ring 65 plugs the hole 70 and permits easy alignment of the screw holes 67 with small pre-drilled holes in the skull (not shown). If small holes were not previously drilled in the skull, the screw holes 67 facilitate drilling holes in the skull before securing the neurocatheter port 51 to the subject's skull 66.

After the neurocatheter port 51 is screwed to the skull 66 the wound is closed in a conventional manner. The tapered shape of the housing 52 in combination with its open flared end 55 facilitate insertion of a needle 63 though the covering skin 64 into and through the septum 54 to access the reservoir 58 of the implanted neurocatheter port 51.

Although the invention has been described by making detailed reference to certain specific embodiments, such detail is intended to be instructive rather than restrictive. It will be appreciated by those skilled in the art that many variations may be made in a structure and mode of operation without departing from the spirit and scope of the invention as disclosed in the teachings herein.

What is claimed is:

1. An implantable port comprising:
   a housing having a base and an open flared end leading to an inlet of an enclosed housing portion which communicates with a reservoir housed therein;
   an outlet in communication with said reservoir;
   said inlet having a selected width;
   a septum mounted in the mouth of said inlet substantially perpendicular to said base; and
   said flared end having a shaped guide surface to facilitate the insertion of a needle into said inlet through said septum, said guide surface being at least twice as wide and twice as long as the width of said inlet.

2. An implantable port according to claim 1 further comprising suture receiving apertures defined on said flared end.

3. An implantable port according to claim 1 wherein said inlet has a selected height and said housing has a low profile having a height not exceeding three times the height of said inlet and said guiding surface being at least four times as wide as the width of said inlet.

4. An implantable port according to claim 3 wherein the height and width of said inlet is less than 0.15 inches.

5. An implantable port according to claim 3 wherein the enclosed housing portion is substantially narrower than said flared end and is tapered away from said flared end.

6. An implantable port according to claim 3 further comprising suture receiving apertures defined on said flared end.

7. An implantable port according to claim 1 wherein said outlet projects from an end of said housing opposite said flared end and proximate said base of said housing; and
further comprising a selectively sized catheter connected to said outlet.

8. An implantable port according to claim 7 wherein said inlet has a diameter greater than 0.10 inches and said catheter has an interior diameter less than four times the inlet diameter.

9. An implantable port according to claim 1 wherein said outlet projects downwardly from said base of said housing; and
further comprising a selectively sized neurocatheter connected to said outlet.

10. An implantable port according to claim 1 wherein said height and width of said inlet are not greater than 0.10 inches.

11. An implantable port according to claim 1 wherein said enclosed housing portion houses a second reservoir;
a second inlet having a selected width communicating with said second reservoir;
a second outlet communicating with said second reservoir;
a second septum mounted in the mouth of said second inlet substantially perpendicular to said base; and
said flared end having a second shaped guide surface to facilitate the insertion of a needle into said second inlet through said second septum, said second guide surface being at least twice as wide and twice as long as the width said second inlet.

12. An implantable port according to claim 11 wherein said inlets are round and have diameters less than 0.15 inches.

13. An implantable port according to claim 11 wherein at least one of said inlets is round and has a diameter not greater than 0.10 inches.

14. An implantable port comprising:
a housing including a hollow body having a selectively defined interior and a radially inwardly projecting lip which defines an inlet;
a hollow core having an exterior selectively configured for mating insertion in an interference fit within the selectively defined interior of said hollow body behind said lip;
a septum being selectively sized to engage said radially inwardly projecting lip of said hollow body; and
said septum and said hollow core being disposed within said hollow body such that said septum is axially compressed between said hollow core and said lip and is thereby forcibly deformed to project into both said inlet and said hollow core whereby said interference fit maintains said septum and said hollow core in place within said housing.

15. An implantable port according to claim 14 wherein said hollow body interior is cylindrical having a selected interior diameter dimension ID and said core exterior is cylindrical having a selected outer diameter dimension OD such that OD is slightly larger than ID to define said interference fit between said hollow core and said hollow body.

16. An implantable port according to claim 15 wherein said hollow body and said hollow core are made of polyetherimide and the difference between ID and OD is 0.002 inches ±0.0005 inches.

17. An implantable port according to claim 16 wherein said inlet has a diameter less than 0.15 inches and the portion of said septum, compressed between said hollow core and said lip, is compressed 0.020–0.025 inches from an uncompressed state.

18. An implantable port according to claim 14 wherein:
said housing has a base and an open flared end leading to said inlet;
said inlet has a selected width;
said septum is mounted in the mouth of said inlet substantially perpendicular to said base; and
said flared end has a shaped guide surface to facilitate the insertion of a needle into said inlet through said septum, said guide surface being at least twice as wide and twice as long as the width of said inlet.

19. An implantable port according to claim 18 further comprising suture receiving apertures defined on said flared end.

20. An implantable port according to claim 18 wherein:
said hollow core includes a reservoir into which said septum partially projects and an outlet extending rearwardly from said core proximate said base of said housing;
said outlet communicating with said reservoir; and
further comprising a selectively sized catheter connected to said outlet.

21. An implantable port according to claim 20 wherein said inlet has a diameter greater than 0.10 inches and said catheter has an interior diameter less than four times said inlet diameter.

22. An implantable port according to claim 18 wherein:
said hollow core includes a reservoir into which said septum partially projects;
said housing includes an outlet which projects downwardly from said base of said housing;
said outlet communicating with said reservoir via an aperture defined in said core; and
further comprising a selectively sized neurocatheter connected to said outlet.

23. An implantable port according to claim 18 wherein said inlet has a selected height and said housing has a low profile having a height not exceeding three times the height of said inlet and said guiding surface being at least four times as wide as the width of said inlet.

24. An implantable port according to claim 23 wherein said width and height of said inlet are less than 0.15 inches.

25. An implantable port according to claim 14 wherein said inlet is round and has a diameter not greater than 0.10 inches.

26. A method for implanting an implantable port on the fascia under the skin of a living creature, the port having a tapered body with a narrow end and a flared end which is substantially wider than said narrow end, the flared end having suture receiving means, comprising:
making an incision in the skin;
inserting the implantable port, narrow end first, beneath the skin;
suturing only the flared end of the implanted port to the fascia; and
closing the incision.

27. A method according to claim 26 wherein said sutures are made with biodegradable material which permits migration of said port due to the growth after implantation.

* * * * *